(12) United States Patent
Chen et al.

(10) Patent No.: US 10,632,232 B2
(45) Date of Patent: Apr. 28, 2020

(54) DEGRADABLE IRON-BASE ALLOY SUPPORT

(71) Applicant: Lifetech Scientific (Shenzhen) Co., Ltd., Shenzhen (CN)

(72) Inventors: Liping Chen, Shenzhen (CN); Hongtao Sun, Shenzhen (CN); Deyuan Zhang, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 123 days.

(21) Appl. No.: 15/534,406

(22) PCT Filed: Dec. 2, 2015

(86) PCT No.: PCT/CN2015/096212
§ 371 (c)(1),
(2) Date: Jun. 8, 2017

(87) PCT Pub. No.: WO2016/107366
PCT Pub. Date: Jul. 7, 2016

(65) Prior Publication Data
US 2017/0340780 A1    Nov. 30, 2017

(51) Int. Cl.
*A61L 31/02*  (2006.01)
*A61L 31/10*  (2006.01)
(Continued)

(52) U.S. Cl.
CPC ............ *A61L 31/022* (2013.01); *A61L 31/02* (2013.01); *A61L 31/041* (2013.01);
(Continued)

(58) Field of Classification Search
CPC ...... A61L 31/022; A61L 31/02; A61L 31/041; A61L 31/10; A61L 31/047; A61L 31/043;
(Continued)

(56) References Cited

U.S. PATENT DOCUMENTS 7,638,158 B2 * 12/2009 Byun ...................... A61L 31/10
                                                              427/2.1
10,058,639 B2 * 8/2018 Zhang .................. A61L 31/022
(Continued)

*Primary Examiner* — Paul B Prebilic
(74) *Attorney, Agent, or Firm* — Raymond Sun

(57) ABSTRACT

A degradable iron-based alloy stent comprises an iron-based alloy substrate and a degradable polymer in contact with the surface of the substrate. The weight-average molecular weight of the degradable polymer is in the range of $[1, 100]*10^4$, and the polydispersity index of the degradable polymer is in the range of $(1.0, 50]$. The degradable polymer is selected from a degradable polyamino acid that can generate an acidic amino acid after degradation; or a mixture of the degradable polyamino acid and a degradable polyester, or a copolymer of monomers of the two; or a mixture of the degradable polyamino acid and a degradable polymer that does not generate acidic products after degradation, or a copolymer of the monomers of the two; or a mixture of the degradable polyamino acid, the degradable polyester and the degradable polymer that does not generate acidic products after degradation, or a copolymer of monomers of the three, or a mixture of a copolymer of monomers of any two of the three with the remaining one. The numerical ranges are in conformity with mathematical knowledge, i.e. [a, b] means being greater than or equal to a and being less than or equal to b; (a, b] means being greater than a and less than or equal to b; [a, b) means being greater than or equal to a, less than b, a redundant description will not be provided for the similarity text below.

3 Claims, 1 Drawing Sheet

(51) Int. Cl.
*A61L 31/16* (2006.01)
*A61L 31/04* (2006.01)
*A61L 31/06* (2006.01)

(52) U.S. Cl.
CPC ............. *A61L 31/043* (2013.01); *A61L 31/06* (2013.01); *A61L 31/10* (2013.01); *A61L 31/16* (2013.01)

(58) Field of Classification Search
CPC ... A61L 31/06; A61L 2420/06; A61L 2420/08
See application file for complete search history.

(56) References Cited

U.S. PATENT DOCUMENTS

| | | | | |
|---|---|---|---|---|
| 2005/0208091 | A1* | 9/2005 | Pacetti | A61L 31/06 424/423 |
| 2005/0251249 | A1* | 11/2005 | Sahatjian | A61L 31/10 623/1.46 |
| 2006/0134166 | A1* | 6/2006 | Luthra | A61L 27/22 424/422 |
| 2007/0224244 | A1* | 9/2007 | Weber | A61L 27/047 424/426 |
| 2008/0035243 | A1* | 2/2008 | Breitenkamp | A61L 27/04 148/240 |
| 2009/0036978 | A1* | 2/2009 | Kleiner | A61L 31/10 623/1.49 |
| 2010/0076544 | A1* | 3/2010 | Hoffmann | A61L 31/022 623/1.15 |
| 2011/0274744 | A1* | 11/2011 | Picart | A61L 15/28 424/445 |
| 2012/0271396 | A1* | 10/2012 | Zheng | A61F 2/82 623/1.2 |
| 2012/0323311 | A1* | 12/2012 | McClain | A61L 31/10 623/1.42 |

* cited by examiner

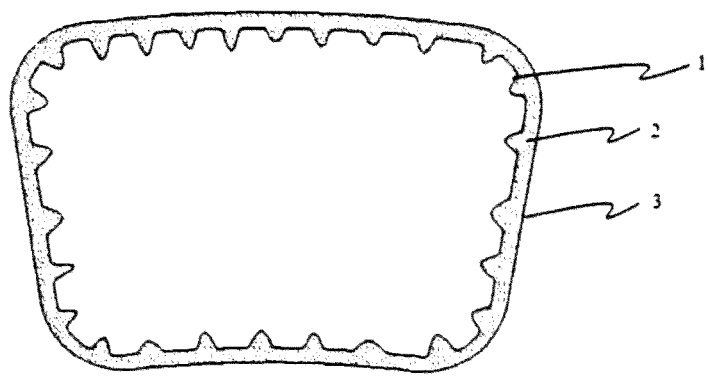

DEGRADABLE IRON-BASE ALLOY SUPPORT

TECHNICAL FIELD

The present disclosure is directed to the field of degradable implantable medical devices and relates to a rapidly degradable iron-based alloy stent.

BACKGROUND

At present, implantable medical devices are typically made of metal and alloys, ceramics, polymers and related composites thereof wherein metal material-based implantable medical devices are especially favored for their superior mechanical properties, such as high strength and high toughness.

Iron, as an important element in the human body, is involved in many biochemical processes, such as oxygen transportation. Easily-corroded pure iron stents, such as Peuster M which were made by laser engraving methods and similar to the clinically used metal stents in shapes were implanted into the descending aorta of 16 New Zealand rabbits. The results of this animal experiment show that there is no thrombosis within 6-18 months, nor adverse events, and it is confirmed from pathological examination that there was no inflammatory response to the local vascular wall, no significant proliferation of smooth muscle cells, which primarily indicates that the degradable iron stents are safe and reliable, and have good application prospects. However, the study found that the pure iron in the body corroded at a low rate, and could not meet the clinical requirement of time for degradation of the degradable stems. Thus, there is a need to improve the corrosion rate of the iron.

Technical Problem

Meanwhile, the study found that the pure iron in the body is corroded at a low rate, and cannot meet the clinical requirement of time for degradation of the degradable stents. Thus, there is a need to improve the corrosion rate of the iron.

Solution for the Problem

Technical Solution

The technical problem to be solved by the present disclosure is to provide a degradable iron-based alloy stent which, when implanted into the body, retains good mechanical properties at an early stage, as well as can be quickly corroded in view of the defects of the prior art.

As the first technical solution of the present disclosure, the degradable iron-based alloy stent comprises an iron-based alloy substrate and a degradable polyamino acid in contact with the surface of the substrate, and the degradable polyamino acid can generate an acidic amino acid after degradation. The weight-average molecular weight of the degradable polymer is in the range of $[1,100]*10^4$, and the polydispersity index of the degradable polymer is in the range of [1.0, 50].

As the second technical solution of the present disclosure, the degradable iron-based alloy stent includes an iron-based alloy substrate and a degradable polymer in contact with the surface of the substrate, the degradable polymer includes a mixture of a polyamino acid that can generate an acidic amino acid after degradation and a degradable polyester, or a copolymer of the degradable polyamino acid monomer with the degradable polyester monomer, and the weight-average molecular weight of the degradable polymer is in the range of $[1,100]*10^4$, and the polydispersity index of the degradable polymer is in the range of [1.0, 50].

As the third technical solution of the present disclosure, the degradable iron-based alloy stent includes an iron-based alloy substrate and a degradable polymer in contact with the surface of the substrate, the degradable polymer includes a mixture of a polyamino acid that can generate an acidic amino acid after degradation and a degradable polymer that does not generate acidic products after degradation, or a copolymer of the monomer of the degradable amino acid and the monomer of the degradable polymer that does not generate acidic products after degradation. The degradable polymer that does not generate acidic products after degradation may be starch, cellulose, polysaccharide, chitin, chitosan or derivatives thereof. The weight-average molecular weight of the degradable polymer is in the range of $[1,100]*10^4$, and the polydispersity index of the degradable polymer is in the range of (1.0, 50].

As the fourth technical solution of the present disclosure, the degradable iron-based alloy stent includes an iron-based alloy substrate and a degradable polymer in contact with the surface of the iron-based alloy substrate. The degradable polymer includes a mixture of a degradable polyamino acid that can generate an acidic amino acid after degradation, a degradable polyester and a degradable polymer that does not generate acidic products after degradation, or a copolymer of the degradable polyamic acid monomer and the degradable polyester monomer and a degradable polymer monomer that does not generate acidic products after degradation, or a mixture of the copolymer of monomers of any two of the degradable polyamino acid, the degradable polyester and the degradable polymers that does not generate acidic products after degradation and the remaining one. The degradable polyamino acid is one that can generate an acidic amino acid after degradation. The weight-average molecular weight of the degradable polymer is in the range of $[1,100]*10^4$, and the polydispersity index of the degradable polymer is in the range of (1.0, 50].

The iron-based alloy substrate according to the present disclosure refers to an iron-based alloy bare stem, which is prepared from pure iron or medical iron-based alloy. Nutrient elements and harmless elements, or less toxic elements in the body, e.g. at least one of c, N, O, S, P, Mn, Pd, Si, W, Ti, Co, Cr, Cu and Re can be doped into pure iron to form the medical iron-based alloy.

The numerical ranges are in conformity with mathematical knowledge, i.e. [a, b] means being greater than or equal to a and being less than or equal to b; (a, b] means being greater than a and less than or equal to b; [a, b) means being greater than or equal to a, less than b, a redundant description will not be provided for the similarity text below.

In the second to fourth technical solutions described above, the degradable polymer in contact with the surface of the substrate comprises a mixture of at least two polymers, the weight-average molecular weight of each degradable polymer is in the range of $[1,100]*10^4$, and the polydispersity index of the degradable polymer is in the range of (1.0, 50]. Taking the second technical solution as an example, in which the degradable polymer in contact with the substrate includes a mixture of a polyamino acid that can generate an acidic amino acid after degradation and a degradable polyester, and the weight-average molecular weight of the polyamino acid and the degradable polyester is in the range of [1,100]*10⁴, and the polydispersity index of the degradable polymer is in the range of [1.0,50].

The rapid corrosion refers to the ability of the degradable polymer to accelerate the corrosion of the iron-based alloy substrate, so that the iron-based alloy substrate can be completely corroded within 10 years after being implanted into the body.

The complete corrosion means that the mass loss rate of the iron-based alloy stent is greater than or equal to 90%.

The complete corrosion is characterized by a mass loss test of an animal experiment. The mass loss test was performed by implanting an iron-based alloy stent of an iron-based alloy substrate (i.e., a bare stent that does not include a degradable polymer) of $M_0$ into the abdominal aorta of a rabbit, and cutting out the iron-based alloy stent and the tissue at which it is located implanted into the animal at a predetermined observation time point. Then the tissue and the stent are soaked in a solution of certain concentration (e.g. 1 mol/L sodium hydroxide solution) to decompose the tissue, and the stem is removed from the solution and placed in a solution of a certain concentration (such as a 3% of tartaric acid solution, and/or an organic solution) for ultrasonication, so that the corroded products on the surface of the stent all fall off or are dissolved in the solution. The remaining stent is removed from the solution, cried and weighed, and the mass is $M_t$. The mass loss rate W is represented by a percentage that the difference of the weight loss of the corrosion-cleaned stent accounts for the weight of the iron-based alloy substrate, as shown in Equation 1-1:

$$W=[(M_0-M_1)/M_0]\times100\% \qquad \text{(Equation 1-1)}$$

W—mass loss rate
$M_1$—the remaining mass of the corroded stent
$M_0$—mass of the iron-based alloy substrate When the stent mass loss rate W is greater than or equal to 90%, this indicates that the iron-based alloy stent is completely corroded.

It is needed to determine the early good mechanical properties of the stem implanted into the body according to the specific clinical requirements. In general, "early" refers to implantation within 1 month, or within 3 months, or within 6 months. The mechanical properties can be verified by animal experiments. It is indicated by early OCT follow-up or radial support force test. In an OCT follow-up, there is no significant difference between the area around the stent and the area of the just implanted stem, or the radial support force is above 23.3 kPa (175 mm Hg) in the radial support force test, indicating that the stent has good mechanical properties when implanted in the body at an early stage.

In the aforementioned four technical solutions, the mass ratio of the iron-based alloy substrate to the degradable polymer is in the range of [1, 200]. Further, the mass ratio of the iron-based alloy substrate to the degradable polymer may be in the range of [5, 50].

In the aforementioned four kinds of technical solutions, the degradable polymer is coated on the surface of the iron-based alloy substrate in the form of a coating.

In the aforementioned first to fourth technical solutions, the iron-based alloy base has a wall thickness in the range of [30, 50) μm, and the degradable polymer coating has a thickness in the range of [3, 5) μm, or [5, 10) μm, or [10, 15) μm, or [15, 20] μm.

In the aforementioned first to fourth technical solutions, the iron-based alloy base has a wall thickness in the range of [50,100) μm, and the degradable polymer coating has a thickness in the range of [5, 10) μm, or [10, 15) μm, or [15, 20) μm, or [20, 25] μm.

In the aforementioned first to fourth technical solutions, the iron-based alloy base has a wall thickness in the range of [100, 200) μm, and the degradable polymer coating has a thickness in the range of [10, 15) μm, or [15, 20) μm, or [20, 25) μm, or [25, 35] μm.

In the aforementioned first to fourth technical solutions, the iron-based alloy base has a wall thickness in the range of [200, 300] μm, and the degradable polymer coating has a thickness in the range of [10, 15) μm, or [15, 20) μm, or [20, 25) μm, or [25, 35) μm, or [35, 45] μm.

In the aforementioned first to fourth technical solutions of the present disclosure, the degradable polyamino acid may be a blend of either or both of polyaspartic acid and polyglutamic acid or a copolymer of monomers of the two.

En the aforementioned second and fourth technical solutions, the coating contains a degradable polyester which may be a blend of one or more of polylactic acid, polyglycolic acid, polybutylene succinate, poly (β-hydroxybutyrate). polycaprolactone, polyethylene adipate, polylactic acid-glycolic acid copolymer, polyhydroxybutyrate copolymer, polyhydroxyalkyl alcohol ester, poly (β-malate) or a copolymer of at least two monomers thereof.

Further, in the aforementioned second technical solution, the mass ratio of the degradable polyamino acid to the degradable polyester or the ratio of the comonomers of the two is in the range of [1:1, 10:1].

In the aforementioned third technical solution of the present disclosure, the degradable polymer that does not generate acidic products after degradation may be starch, cellulose, polysaccharide, chitin, chitosan or derivatives thereof and the like, the ratio of the amino acid to the degradable polymer that does not generate acidic products after degradation or the ratio of the comonomers of the two is in the range of [1:1, 10:1].

In the aforementioned fourth technical solution of the present disclosure, the content of the degradable polyamino acid, the degradable polyester and the degradable polymer that does not generate acidic products after degradation or the content of the comonomers of the three is respectively [10%, 80%], [10%, 80%], [10%, 60%].

In the aforementioned first to fourth technical solutions of the present disclosure, the iron-based alloy substrate may further be provided with an aperture or recess, and the degradable polymer is provided therein; or the iron-based alloy substrate has an internal cavity, in which the degradable polymer is filled. When the degradable polymer in contact with the surface of the iron-based alloy substrate is a mixture of at least two polymers, as for the polymers which are mixable with each other, the mixture may be prepared by mixing at least two polymers, contacting the blend with the iron-based alloy in the form of a coating or the aforementioned manner with an iron-based alloy substrate or forming a coating on one side of the iron-based alloy substrate with one of the polymers, and then laminating on the coating successively a coating formed from the remaining polymers, or by providing different polymer coatings in different regions of the surface of the iron-based alloy. As for the polymers which are not mixable with each other, the mixture may be prepared by forming a coating on the surface of the iron-based alloy substrate with one of the polymers, and then laminating on the coating successively a coating formed from the remaining polymers, or by providing different polymer coatings in different regions of the surface of the iron-based alloy substrate.

In the first to fourth technical solutions of the present disclosure, the degradable polymer may be mixed with an active drug, and the mass ratio of the degradable polymer to the drug is in the range of [0.1, 20]. The active drug may be a drug that inhibits angiogenesis such as paclitaxel, rapamycin and derivatives thereoff, or antiplatelet drugs selected from cilostazol, or antithrombotic drugs such as heparin, or anti-inflammatory drugs such as dexamethasone, or a mixture of the aforementioned drugs. Further, the mass ratio of the degradable polymer to the drug is in the range of [0.5, 10].

THE BENEFICIAL EFFECTS OF THE INVENTION

Beneficial Effects:

Compared with the prior art, the degradable iron-based alloy stent provided by the invention adopts the specific degradable polymer to primarily subject the iron-based alloy substrate to chemical reaction under the action of the degradable polymer, so as to accelerate the corrosion rate of iron, as well as meet the clinical requirements of the early mechanical properties of the stem.

BRIEF DESCRIPTION OF THE DRAWINGS

FIG. 1 is a schematic cross-sectional view of an iron-based alloy stent and a coated support provided in example 5 of the present disclosure.

BEST EXAMPLE OF THE INVENTION

Best Implementation for the Invention

It is to be noted that, on the basis of an animal experiment for the degradable iron-based alloy stent provided by the present disclosure, it can be verified that the iron-based alloy stents are capable of rapidly corroding the iron-based alloy stent under the action of a degradable polymer, and it can be determined whether the iron-based stent is rapidly corroded or not primarily through early mechanical properties, and whether it is completely corroded in a certain period by the mass loss test.

Specifically, the iron-based alloy stent containing the degradable polymer is implanted into the animal and tested respectively at predetermined observation time points. For example, an OCT follow-up test for the stem being implanted in the body for 3 months. There is no significant difference between the area around the stem and the area of the just implanted stent. Or the animals are euthanised, the stent and the tissue at which it is located are removed from the body, and the stem and the blood vessel at which it is located are subjected to a radial support force test to determine whether the stem satisfies the early mechanical properties or not. The stent sample is removed after it has been implanted for 2 years to test the stent mass loss to determine whether the stent had been completely corroded or not.

The test for the radial support force may be performed using the radial support force tester RX550-100 produced by MSI company, including removal of the stent implanted in the animal with the vessel at a predetermined observation time point, and the test is then carried out to obtain the radial support force.

The complete corrosion is characterized by a mass loss test of an animal experiment. The test is performed by implanting an iron-based alloy stent of an iron-based alloy substrate (i.e., a bare stent that does not include a degradable polymer) of $M_0$ into the abdominal aorta of a rabbit, and cutting out the iron-based alloy stent and the tissue at the implant location at a predetermined observation time point. Then the tissue and the stent are soaked in a solution of a certain concentration e.g., 1 mol/L sodium hydroxide solution) to decompose the tissue, and the stent is removed from the solution and placed in a solution of a certain concentration (such as a 3% of tartaric acid solution, and/or an organic solution) for ultrasonication, so that the corroded products on the surface of the stent all fall off or are dissolved in the solution. The remaining stent is removed from the solution, dried and weighed, and the mass is $M_t$. The mass loss rate W is represented by a percentage that the difference of the weight loss of the corrosion-cleaned stent accounts for the weight of the iron-based alloy substrate, as shown in Equation 1-1:

$$W=[(M_0-M_1)/M_0]\times 100\% \qquad \text{(Equation 1-1)}$$

W—mass loss rate
$M_1$—the remaining mass of the corroded stent
$M_0$—mass of the iron-based alloy substrate When the stem mass loss rate W is greater than or equal to 90%, this indicates that the iron-based alloy stent is completely corroded. The weight-average molecular weight of the degradable polymer and its polydispersity index are detected by an octagonal laser light scattering instrument produced by Wyatt Technology Corporation (WTC).

The degradable iron-based alloy stent provided by the present disclosure will be further described below with reference to the accompanying drawings and examples. It is to be understood that the following examples are merely preferred examples of the invention and are not intended to limit the present invention; any modifications, equivalent replacements and modifications within the spirit and principles of the invention are included within the protection scope of the present disclosure.

Example 1

A pure iron stent comprises a pure iron substrate and a degradable polymer coating coated on the surface of the pure iron substrate, where the mass ratio of the pure iron substrate to the degradable polymer was 10:1. The degradable polymer was polyglutamic acid, the weight-average molecular weight was 15,000, the polydispersity index was 1.5, the wall thickness of the iron substrate was 80-90 μm, and the thickness of the degradable polymer coating was from 10 to 15 μm. The stem was implanted into the abdominal aorta of the rabbit. The stent and the tissue at which it was located were removed from the body after they had been implanted in the body for 3 months for the radial support force test. The test result was 70 kPa. Re-sampling after 2 years, carrying out the mass loss test, the stent mass loss rate was 95%, indicating that the stent had been completely corroded.

Example 2

A degradable polymer coating having a thickness of from 8 to 10 microns was uniformly coated on the surface of a nitrided pure iron bare stent (i.e., a nitrided pure iron substrate) having a wall thickness of from 50 to 70 microns, the mass percentage of the substrate and the degradable polymer was 25, the degradable polymer coating was a polyaspartic acid-lactic acid copolymer coating having a weight-average molecular weight of 100,000 and a polydispersity index of 3, and wherein the aspartic acid was copolymerized with lactic acid by a ratio of 1:1. After the coating was dried, the degradable iron-based alloy stent was prepared. The iron-based alloy stent was implanted into a porcine coronary artery. It was found from an OCT follow-up test for the stem implanted in the body for 3 months that there was no significant difference between the area around the stent and the area of the just-implanted stent. The mass loss test was carried out, and the stent mass loss rate was 92%, indicating that the stent had been completely corroded.

Example 3

A polyglutamic acid coating having a thickness of from of 3 to 5 microns was uniformly coated on the surface of an electrodeposited pure iron (550° C., annealed) bare stent (i.e., electrodeposited pure iron substrate) having a wall thickness of from 40 to 50 microns, and the polyglutamic acid coating was coated with a polycaprolactone (PCL) rapamycin mixed coating having a thickness of from 5-8 microns. The ratio of polycaprolactone to rapamycin was 2:1, the mass ratio of electrodeposited pure iron substrate to the degradable polymer was 35:1, in which the weight-average molecular weight of polycaprolactone was 30,000, the polydispersity index was 1.3, the weight-average molecular weight of the polyglutamic acid was 80,000, the polydispersity index was 1.6, and the mass ratio was 1:1. A degradable iron-based alloy stent was prepared after drying. The stent was implanted into the abdominal aorta of the rabbit and the stem was removed at a corresponding observation time point. The surface of the stent was observed with a microscope and a percentage of the radial support force to the mass loss of the stent was tested. Test results show that the 3-month radial support force was 60 kPa; the mass loss test was carried out after 1 year to find that the stent mass loss rate was 98%, indicating that the stent had been completely corroded.

Example 4

The surface of the outer wall of the carburized iron bare stent (i.e., the carburized iron base) after the heat treatment was coated with a mixed coating of polyaspartic acid and starch. The carburized iron base had a wall thickness of from 140 to 160 microns, the coating had a thickness of from 30 to 35 microns, and the mass ratio of the carburized iron substrate to the degradable polymer was 30:1. The coating was divided into two layers, the bottom layer was a polyaspartic acid having a molecular weight of 400,000, the top layer was a chitosan coating having a molecular weight of 30,0000, and the polydispersity index was 1.2. The mass ratio of the two degradable polymer coatings was 5:1. A degradable iron-based alloy stent was prepared after drying. The stent was implanted into the abdominal aorta of the rabbit and the stent was removed at a corresponding observation time point. The surface of the stent was observed with a microscope and a percentage of the radial support force to the mass loss of the stem was tested. The test results showed that the radial support force of 6 months was 50 kPa, and the mass loss rate of the stent was 93% after 5 years.

Example 5

An iron-manganese alloy bare stent (i.e., ferro-manganese alloy substrate) was polished, so that the surface of the stent was distributed with recesses, as shown in FIG. 1, the stent had a thickness 1 of from 100 to 120 microns, and the surface of the stent 1 was provided with a recess 2. A mixture coating 3 of two layers of degradable polymer was uniformly coated on the surface of the stent 1 and in the recess 2. The coating of the degradable polyester-based polymer was a polyglutamic acid-caprolactone copolymer having a weight-average molecular weight of 500,000 which was copolymerized by a mass ratio of 2:1, and the polymer polydispersity index was 10, the thickness of the coating of the mixture was from 20 to 25 microns, and the mass ratio of the iron-based alloy substrate to the degradable polymer was 40:1. A degradable iron-based alloy stent was prepared after drying. The stent was implanted into the porcine coronary artery, and the stent was removed at a corresponding observation time point. The mass loss rate and the radial support force were tested. The test results of 3 months showed that the radial support force was 60 kPa, it was found from the mass loss test after 4 years that the mass loss rate of the stent was 95%.

Example 6

A degradable polymer coating having a thickness of from 35 to 45 microns was coated relatively uniformly on the surface of a sulfurized iron bare stent (i.e., a sulfurized iron-based alloy substrate) having a wall thickness of from 250 to 270 microns, the coating was divided into two layers, including a bottom layer of chitosan having a molecular weight of 500,000, and a polydispersity index of 10, and a top layer of polyglutamic acid lactic acid-glycolic acid copolymer coating (a copolymerization ratio of 1:1) having a molecular weight of 300,000, and a polydispersity index of 5. The mass ratio of the carburized iron-based alloy substrate to the degradable polymer is 50:1, and the mass ratio of the two coatings is 1:2. A degradable iron-based alloy stent was prepared after drying. The stent was implanted into the porcine abdominal aorta, and the stent was removed at a corresponding observation time point to test the mass loss of the iron-based alloy stem. The test results showed that the radial support force of 6 months was 50 kPa, and the mass loss rate of the stem was 90% after 5 years.

Example 7

A mixed coating of polyaspartic acid and heparin having an average thickness of from 12 to 15 microns was coated on the surface of a carburized iron bare stem (i.e., a carburized iron substrate) having a wall thickness of from 50 to 70 microns, wherein the two were mixed by a ratio of 5:1, the aspartic acid molecular weight was 1 million, the polydispersity index was 20, and the mass ratio of the carburized iron-based alloy substrate to cocoa-degradable polymer was 30. The degradable iron-based alloy stem was implanted into the porcine coronary artery, and the iron-based alloy stent was removed at a corresponding observation time point for the mass loss test and radial support force test. The test results showed that the radial support force of 3 months was 60 kPa, and the mass loss rate of the stent was 98% after 4 years.

Comparative Example 1

A pure iron bare stent (pure iron substrate, i.e., the surface is not covered with any coating) having a wall thickness of from 60 to 70 microns was implanted into the abdominal aorta of the rabbit. After three months, the stent was removed, the radial support force was tested as 120 kPa, the stent was removed after being implanted for 3 years for a mass loss test, and at this time, the mass loss rate of the stent was 25%, indicating that the bare iron stent corrosion rate was slow.

Comparative Example 2

A polylactic acid coating having a thickness of from 25 to 35 microns was coated on a pure iron bare stent (i.e., pure iron substrate) having a wall thickness of from 60 to 70 microns, the mass ratio of the pure iron substrate to the polylactic acid was 10:1, the polylactic acid has a weight-average molecular weight of 15,000 and a polydispersity index of 1.8. An iron-based stent was prepared after drying, which was implanted in the abdominal aorta of a rabbit. The radial support force test result was 20 kPa after 3 months, the mass loss test for the stent showed that the mass loss rate of the stent was 100% after 6 months, indicating that the stent had been completely corroded fast, and the clinically required mechanical properties were not met at an expected time point.

It can be seen from the test results of Examples 1 to 7 and Comparative Examples 1 to 2 that the present invention provides a corrodible iron-based alloy stent having a weight-average molecular weight in the range of [20000, 1 million], and the degradable polymer with a polydispersity index in the range of (1.0, 50] not only achieves a complete corrosion of the iron-based alloy substrate within 10 years of implantation thereof, but also meets the clinical requirements of corrosion cycles of the degradable stent. In an OCT follow-up, there is no significant difference between the area around the stem and the area of the just implanted stent, or the radial support force is above 23.3 kPa (175 mm Hg) in the radial support force test, which has met clinical requirement for mechanical properties of the stent implanted in the body.

The invention claimed is:

1. A degradable iron-based stent, comprising an iron-based substrate and a degradable polymer in contact with the surface of the substrate, wherein:
   the degradable polymer is a polyaspartic acid-lactic acid copolymer coating having a weight-average molecular weight of 100,000 and a polydispersity index of 3;
   wherein the aspartic acid is copolymerized with lactic acid by a ratio of 1:1; and
   the stent has a radial support force of above 23.3 kPa (175 mm Hg) in a radial support force test after the stent has been implanted for 3 months.

2. A degradable iron-based stent, comprising an iron-based substrate and a degradable polymer in contact with the surface of the substrate, wherein:
   the iron-based substrate is an electrodeposited pure iron substrate having a wall thickness of 40 to 50 microns;
   the degradable polymer is a polyglutamic acid coating having a thickness of 3 to 5 microns and is uniformly coated on the surface of the electrodeposited pure iron substrate, and the polyglutamic acid coating is coated with a polycaprolactone (PCL) rapamycin mixed coating having a thickness of 5-8 microns;
   the ratio of polycaprolactone to rapamycin is 2:1;
   the mass ratio of the electrodeposited pure iron substrate to the degradable polymer is 35:1;
   the weight-average molecular weight of polycaprolactone is 30,000 and has a polydispersity index of 1.3;
   the weight-average molecular weight of the polyglutamic acid is 80,000 and has a polydispersity index of 1.6; and
   the stent has a radial support force of 60 kPa in a radial support force test after the stent has been implanted for 3 months.

3. A degradable iron-based stent, comprising an iron-based substrate and a cocoa-degradable polymer in contact with the surface of the substrate, wherein:
   the iron-based substrate is a carburized iron bare stent having a wall thickness of 50 to 70 microns;
   the degradable polymer is a mixed coating of polyaspartic acid and heparin having an average thickness of from 12 to 15 microns, with the polyaspartic acid and the heparin mixed by a ratio of 5:1;
   the molecular weight of the polyaspartic acid is 1 million and the polyaspartic acid has a polydispersity index of 20;
   the mass ratio of the iron-based substrate to degradable polymer is 30; and
   the stent has a radial support force of above 23.3 kPa (175 mm Hg) in a radial support force test after the stent has been implanted for 3 months.

* * * * *